(12) United States Patent
Sakurai et al.

(10) Patent No.: US 8,183,054 B2
(45) Date of Patent: May 22, 2012

(54) INSTRUMENT AND METHOD FOR COLLECTING NUCLEIC ACIDS

(75) Inventors: Toshinari Sakurai, Hitachinaka (JP);
Toshiaki Yokobayashi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 12/869,519

(22) Filed: Aug. 26, 2010

(65) Prior Publication Data

US 2011/0015381 A1 Jan. 20, 2011

Related U.S. Application Data

(62) Division of application No. 10/468,598, filed on Feb. 11, 2004, now abandoned.

(30) Foreign Application Priority Data

Mar. 28, 2001 (WO) .................. PCT/JP01/02577

(51) Int. Cl.
*G01N 1/18* (2006.01)
(52) U.S. Cl. ........................................ 436/178
(58) Field of Classification Search ............ 436/178
See application file for complete search history.

(56) References Cited

U.S. PATENT DOCUMENTS

| | | | |
|---|---|---|---|
| 5,188,730 A | 2/1993 | Kronwald | |
| 5,910,246 A | 6/1999 | Walter et al. | |
| 6,162,356 A | 12/2000 | Ikeda et al. | |
| 6,165,478 A * | 12/2000 | Izutsu et al. | 424/263.1 |
| 6,168,922 B1 | 1/2001 | Burghoff et al. | |
| 6,326,189 B1 * | 12/2001 | Fukuzono et al. | 435/287.2 |
| 6,383,393 B1 * | 5/2002 | Colpan et al. | 210/656 |

FOREIGN PATENT DOCUMENTS

| | | |
|---|---|---|
| EP | 0 268946 | 6/1988 |
| EP | 0 389 063 | 9/1990 |
| JP | 11-127854 | 5/1999 |
| JP | 11-266864 A | 10/1999 |
| JP | 2000-175683 | 6/2000 |
| JP | 2000-350577 | 12/2000 |
| JP | 3663207 | 10/2004 |
| JP | 3619514 | 2/2005 |

OTHER PUBLICATIONS

Machine translation of JP11-266864, Date: Jun. 27, 2008.
Machine translation of JP2000-175683, Date: Jun. 27, 2008.

* cited by examiner

*Primary Examiner* — Bobby Ramdhanie
(74) *Attorney, Agent, or Firm* — Dickstein Shapiro LLP

(57) ABSTRACT

An instrument and a method for conveniently collecting nucleic acids from a biological nucleic acid-containing sample are provided. A nucleic acid-capturing tip having silica-containing solid phases enclosed therein in such a state as being capable of coming into contact with a liquid, wherein the solid phases have a water-flowing regions and the average interval among solid phases in the water-flowing regions is regulated to 25 μm or less.

12 Claims, 7 Drawing Sheets

INSTRUMENT AND METHOD FOR COLLECTING NUCLEIC ACIDS

This application is a divisional of Ser. No. 10/468,598, filed Feb. 11, 2004, now abandoned, the entire disclosure of which is hereby incorporated by reference.

TECHNICAL FIELD

The present invention relates to a device for collecting nucleic acids and particularly, to an instrument collecting nucleic acids from a biological nucleic acid-containing sample. Specifically, the present invention relates to an instrument for collecting nucleic acid components contained in a biological sample in the form of endogenous or exogenous genes from humoral components, wherein the collected nucleic acid components are used for genetic diagnosis.

BACKGROUND ART

A series of breakthroughs achieved in molecular biology has resulted in a wide variety of genomic techniques, providing a large number of disease-inducing genes to be separated and identified. In this context, molecular biological techniques have been introduced in diagnosis and examination in the medical field, not only enabling diagnosis, which could not be implemented in former years, to be successfully made but also considerably reducing the time period (in days) for an examination.

Such rapid progress has been made mainly under the favor of nucleic-acid amplification testing (NAT), especially, the polymerase chain reaction technique (PCR technique: Saiki et al., Science, 239, 487-491 (1988)). Since the PCR technique allows nucleic acids in a solution to be amplified sequence-specifically, for example, the existence of virus, only a trace amount of which is contained in serum, may be indirectly proved by amplifying and detecting the nucleic acids, which are genes of the virus.

Using the PCR technique, however, in routine examination made at clinical sites involves some problems. To address these problems, in particular, it is indicated that the nucleic acid extraction and purification processes is important in pre-processing (Ohshima et al., JJCLA, 22(2), 145-150 (1997)). These problems are induced by inhibitors, known as, for example, hemoglobin in blood and a surface active substance used in the extraction process, which could not be removed in the nucleic acid purification process. The extraction process requires a tedious operation necessary for the technique and a large amount of labor by experts. For this reason, this process disturbs the new introduction of genetic testing into hospital laboratory rooms and it is eagerly desired to automate this proceed.

Similarly, in institutions, where molecular biological researches are conducted, plasmid DNA is commonly used as a substance used for genetic recombination, it is also desired to automate the nucleic acid extraction and purification processes from the standpoint of laborsaving.

A known method for collecting nucleic acids from a biological sample containing nucleic acids in the highly-purified form without containing inhibitors includes the method, which collects the nucleic acids, in such a manner that a surface active substance is caused to act on the biological sample under the existence of protease, separating the nucleic acids, phenol (and chloroform) is mixed with it, aqueous phase-organic phase separation is applied in a centrifuge several times, and collecting the nucleic acids in the form of precipitate from the water phase sample by adding alcohol. However, such a problem has arisen that this method of preparation requires an organic solvent such as phenol, a poisonous substance, in the process or the centrifugation process, or the automation of loading/unloading vessels in the centrifuge and dispensing a centrifuged solution is very difficult.

U.S. Pat. No. 2,680,462 discloses that silica particles capable of binding to the nucleic acids under the presence of a chaotropic substance are used as a solid phase for binding nucleic acids. In the U.S. Pat. No. 2,680,462, the method which collects the nucleic acids in such a manner that a sample containing nucleic acids is added in a reaction vessel with a silica-particle suspension and a guanidine thiocyanate buffer solution as a chaotropic substance and mixed together, a complex composed of the nucleic acids bound to the silica particles is precipitated using a centrifuge, supernatant liquid was removed, a cleaning liquid is added to the remaining complex for cleaning, the re-precipitated complex is cleaned in a ethanol water solution and further cleaned with acetone, acetone is removed off from the complex, and finally a elution buffer is added to the complex, after dried, for eluting the nucleic acids.

In JP-A No. 250681/1995, the method for purifying a DNA extraction liquid using a cartridge vessel having a quadruple-structured filtering member, wherein a glass powder layer is inserted between two glass fiber filters and membrane filters, is disclosed. In JP-A No. 250681/1995, the sample to be purified is extracted in such a manner that a prepared DNA-containing culture is pre-processed and pipetted on a trap filter, and then an elution reagent is added on it to elute plasmid DNA from a cell. In the purification process, the sample to be purified and sodium iodide are added in the cartridge vessel and vacuum-depressurization or centrifugation is applied to the cartridge vessel to absorb the plasmid DNA to the glass powder layer. Next, a cleaning buffer solution is added in the cartridge vessel, vacuum-depressurization or centrifugation is applied for cleaning, and then an elution buffer is added in the cartridge vessel, vacuum-depressurization or centrifugation is applied again to elute the plasmid DNA.

Besides, in JP-A No. 266864/1999, a method and an instrument for purifying nucleic acids using a nucleic acid capturing tip, which has a silica-containing solid phase therein, is disclosed. In this method, the nucleic acid capturing tip is detachably attached to a movable nozzle for liquid suction/discharge, a mixture of a substance for accelerating binding of the nucleic acids to the solid phase, and a nucleic acid-containing sample is aspirated into the nucleic acid capturing tip attached to the movable nozzle for liquid suction/discharge from the given vessel, the liquid is discharged from the nucleic acid capturing tip after the nucleic acids are bound to the solid phase, then a cleaning liquid is aspirated and discharged to clean the inside of the nucleic acid capturing tip, and finally an eluent is aspirated in the cleaned nucleic acid capturing tip to discharge the eluent containing the nucleic acids eluted from the solid phase in the purified sample vessel.

DISCLOSURE OF THE INVENTION

Problem to be Solved

Among prior arts mentioned above, in the method disclosed in JP-A No. 2680462, the use of phenol, a poisonous substance, may be avoided but the centrifugation process is required to separate the silica particles bound to the nucleic acids from the solution, posing a problem in automating the centrifugation process, as in the case of the phenol-based extraction method.

In the method disclosed in JP-A No. 250681/1995, the introduction of the cartridge vessel having a glass powder layer inserted two glass fiber filters and membrane filters enable the vacuum-depressurization process to substitute for the centrifugation process, which can be said to suitable method for automation, though a flow of the solution is limited to one direction, reducing an efficiency in contacting the plasmid DNA or elution buffer with the glass powder layer, which in turn, affects collection efficiency.

Further, in the method disclosed in JP-A No. 266864/1999, by the nucleic acid capturing tip internally having a solid phase is detachably attached to the movable nozzle for liquid suction/discharge to force the solution to flow bi-directionally, the contact efficiency between the nucleic acids or the elution buffer and the solid phases is improved, facilitating automation, while configuration examples of the nucleic acid capturing tip were described but not more preferable modes of usage.

The object of the present invention is to provide an instrument and a method for collecting rapidly and easily the nucleic acids at a high reliability from the nucleic acid containing sample, and especially, the instrument and the method suitable for collecting the nucleic acid components contained in a biological sample.

Further, another object of the present invention is to provide the instrument and the method suitable for automation for collecting the nucleic acids from the nucleic acid containing sample, and especially, the instrument and the method suitable for automatically collecting the nucleic acids contained in the biological sample.

Means to Solve the Problem

The instrument for collecting the nucleic acids according to the present invention is preferably the nucleic acid capturing tip. The present invention is characterized in that the instrument for collecting the nucleic acids internally having the silica-containing solid phase, which may come into contact with a liquid, having a water-flowing regions, wherein an average interval among the solid phases in the water-flowing regions is 25 μm or less.

The instrument for collecting the nucleic acids according to the present invention using the nucleic acid capturing tip internally having the silica-containing solid phase having the water-flowing regions, wherein the average interval among the solid phases in the water-flowing regions is 25 μm or less, comprises:

a first step (Step 1) for mixing a first reagent to separate nucleic acids from a nucleic acid containing sample, accelerating separation of the nucleic acids;

a second step (a) (Step 2a) for mixing a second reagent with the liquid containing separated nucleic acids, aspirating the mixture into the nucleic acid capturing tip by changing a pressure, applied to come into contact with the solid phase, and then discharging the mixture;

a second step (b)(Step 2b) for aspirating a second reagent into the nucleic acid capturing tip by changing a pressure applied to come into contact with the solid phase, and dicharging to rinse the solid phase;

a third (a) step (Step 3a) for aspirating a third reagent in the nucleic acid capturing tip by changing the pressure applied tip, making the third reagent into contact with the solid phase, and then discharging the mixture to remove the first and/or the second reagents remaining in the nucleic acid capturing tip;

a third (b) step (Step 3b) for blowing air into the nucleic acid capturing tip, accelerating removal of the third reagent from the tip;

a fourth step (Step 4) for aspirating a fourth reagent in the nucleic acid capturing tip by changing the pressure applied, making the fourth reagent into contact with the solid phase, and then discharging the mixture to rinse the remaining third reagent out; and a fifth step (Step 5) for aspirating a fifth reagent into the nucleic acid capturing tip by changing the pressure applied to dissolute the nucleic acids from the solid phase, making the fifth reagent into contact with the solid phase, and then discharging the mixture. Note that in the case that the solid phase is composed of a granular substance or a fibrous substance, an average pore size means an average interval, which is characterized in that it is 25 μm or less.

According to a preferred embodiment, the nucleic acid capturing tip is replaced with a new one every time the sample to be processed is changed. In each of Steps 2a, 2b, 3a, 4, and 5, the operations of discharging the aspirated solution into a given vessel and of aspirating the discharged solution into the nucleic acid capturing tip are repeated to ensure making the solution into contact with the solid phase at a high efficiency. Note that since malfunctions such as produced bubbles and increased suction resistance during the suction operation occur as the whole amount of solution is discharged when the solution is discharged in Steps 2a and 2b, it is preferable to control the steps so that the solid phase may always keep contact with the solution without the whole amount of solution discharged.

BEST MODE FOR CARRYING OUT OF THE INVENTION

Figure 1:
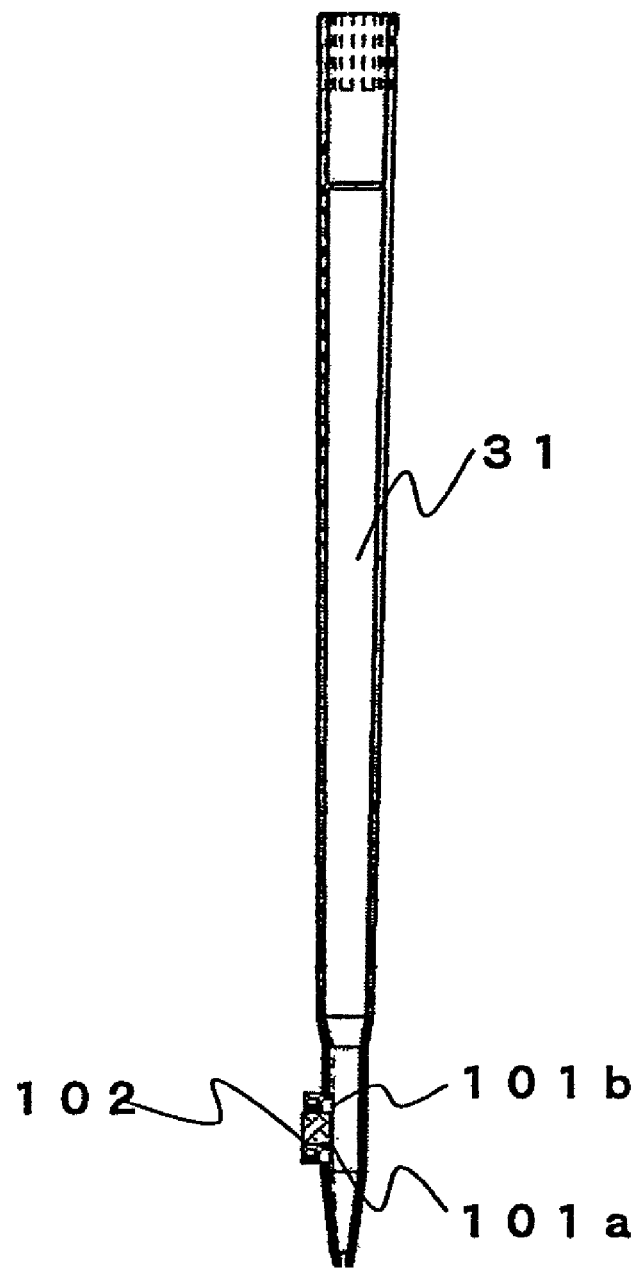
FIG. 1 is a view showing a nucleic acid capturing tip, which is a embodiment according to the present invention.

For a nucleic acid containing sample, any of living-body samples such as while blood, serum, sputum, and urine, biological samples such as cultured cells and cultured bacteria, and substances containing nucleic acids retained in a gel, which has undergone electrophoresis, or nucleic acids such as reaction products by a DNA amplifying enzyme or coarsely-purified nucleic acids may be used. Note that the nucleic acids referred to herein, include deoxyribonucleic acids (DNA) and ribonucleic acids (RNA) having a double strand structure, a single strand structure, a partially-double strand structure, or a partially-single strand structure.

For the solid phase enclosed in the nucleic acid capturing tip, any of substances or products containing silicon dioxide such as glass particles, silica particles, quartz filters and its fractured granules, silica wool, and diatomite or products such as plastics of which surfaces are coated with silica may be used. It is required that the solid phase be retained in the tip throughout its use and disposed so that it may have water-flowing regions in the tip, wherein the water-flowing regions preferably take a continuous form. In reference to the shape of the solid phase, it may be any of porous, granular, and fibrous types, wherein an average interval among the solid phases in the water-flowing regions means an average size of its pore in the case of it being porous type while it means an average interval among the granules or the fibers in the case of it being granular or fibrous type, each of which is narrower than 25 μm (included). The desired solid phase in the present invention is silica wool and preferably, retaining material made of sintered silica particles is disposed on both sides of it to control the average interval among the silica wools used as the solid phase.

Note that the average interval among the silica wools referred to herein indicates the average interval among the silica wools, which are assumed to be cylindrical, formed when they are uniformly disposed in a space, and it's size is determined depending on the volume, cross section, and length of the space, in which the silica wools are disposed, and the weight, relative density, and average diameter of the disposed silica wools.

For example, in the case of the space, in which the silica wools are disposed, having a cylindrical shape with a radius of 1.5 mm, and of which portion, where the silica wools are disposed, has a length of h, the average interval I among silica wools can be calculated form the following formula, assuming that the relative density of the silica wools is 2.22 g/cm$^3$, the average radius of the silica wools is 4.5 μm, the total volume of the silica wools disposed is 5 mg:

$$l[m]=5.04\times10^{-4}\cdot h^{1/2}-9.0\times10^{-6}$$

For the instrument for forcing the nucleic acid capturing tip to aspirate and discharge the solution by changing the pressure applied, any instrument including manual pipette or syringe, but not limited to them, may be used provided that it has a shape fitting to one end of the nucleic acid capturing tip and can apply a change in pressure intentionally, though it is preferable that it is combined with an automatic device because the amount of aspirated solution, the amount of discharged solution, suction speed, and discharge speed, and other factors must be controlled to collect the nucleic acids stably.

For the reagent to be used in Step 1, any of those, which can accelerate the separation of the nucleic acids from the nucleic acid containing sample, may be used but the use of any of those with high viscosity is not desirable. In addition, in the case of the nucleic acids to be collected being RNA, it is preferable that a RNase inhibitor is added or guanidine thiocyanate is used to prevent ribonuclease (RNase) from acting.

For the reagent to be used in Step 2a, any of those, which can accelerate the bond of the nucleic acids to the silica-containing solid phase, may be used and a reagent generally called a chaotropic reagent may be used. In the case of the nucleic acids to be collected being RNA, it is preferable that guanidine thiocyanate is used for the same reason as that of Step 1 and further preferably, its final concentration is 3 mol/L or higher and its final pH value indicates acidity.

For the reagent to be used in Step 3a, any of those, which can remove the substance capable of accelerating the bond of the nucleic acids to the solid phase used in Step 2 while keeping the bond of them to the solid phase, may be used, and the method, which uses, as a reagent, 70% or higher concentration of ethyl alcohol or isopropyl alcohol, is known, but it has been elucidated that these substances may adversely affect in the case that the collected nucleic acids are used in the methods such as PCR, so it is preferable that they are used at a concentration as low as they can retain its intrinsic function. According to the preferred embodiment of the present invention, from the standpoints mentioned above, 50% ethyl alcohol with 25 mmol/L potassium acetate contained is used.

For the reagent to be used in Step 4, any of those, which can remove the alcohol used in Step 3 while keeping the bond of the nucleic acids to the solid phase as stably as possible, may be used, but it must be avoided to carry over the reagent used in Step 3 to the last step. According to the preferred embodiment of the present invention, from the standpoint mentioned above, 50 mmol/L potassium acetate with its temperature of 20° C. or lower is used.

For the reagent to be used in Step 5, any of substances, which can have action of dissolving the nucleic acids from the solid phase, may be used, and the method, which uses a low concentration of salt solution or deionized water, is known. According to the preferred embodiment of the present invention, 10 mmol/L bicine (pH8.5) and 0.1 mmol/L EDTA are used.

Example

Now, referring to FIG. 1, the instrument for collecting the nucleic acids, which is a preferred embodiment according to the present invention, is described below.

FIG. 1 is a view showing the configuration of the nucleic acid capturing tip. The upper end of the nucleic acid capturing tip 31 has an inside diameter which allows the upper end to be hermetically fitted to the tip of a connection nozzle of the device for generating a change in pressure or an automatic device, wherein the nucleic acid capturing tip is shaped so that its inside diameter becomes gradually narrow toward the bottom end. The nucleic acid capturing tip 31 is composed of a transparent or semitransparent synthetic resin. On the tip side of the tip 31, disk-shaped blocking members 101a and 101b for preventing the solid phase from running out and for limiting the average interval among the solid phases are disposed by pressing in the tip 31 from its top end so that the solid phase 102 is sandwiched between them, allowing the solid phases 102 to keep the given average interval. These blocking members 101a and 101b have a large number of pores, through which a liquid or gas can pass easily, of which size is one capable of blocking run-out of the solid phase 102.

As a material for the blocking members 101a and 101b, silica particles of about 0.1 mm of size sintered into a shape capable of fitting to an inside diameter of the nucleic acid capturing tip 31 at a given point is used.

For the solid phase, 5 mg of silica wools (Toshiba Chemical, Grade B, diameter: 6-12 μm) is used.

Figure 2:
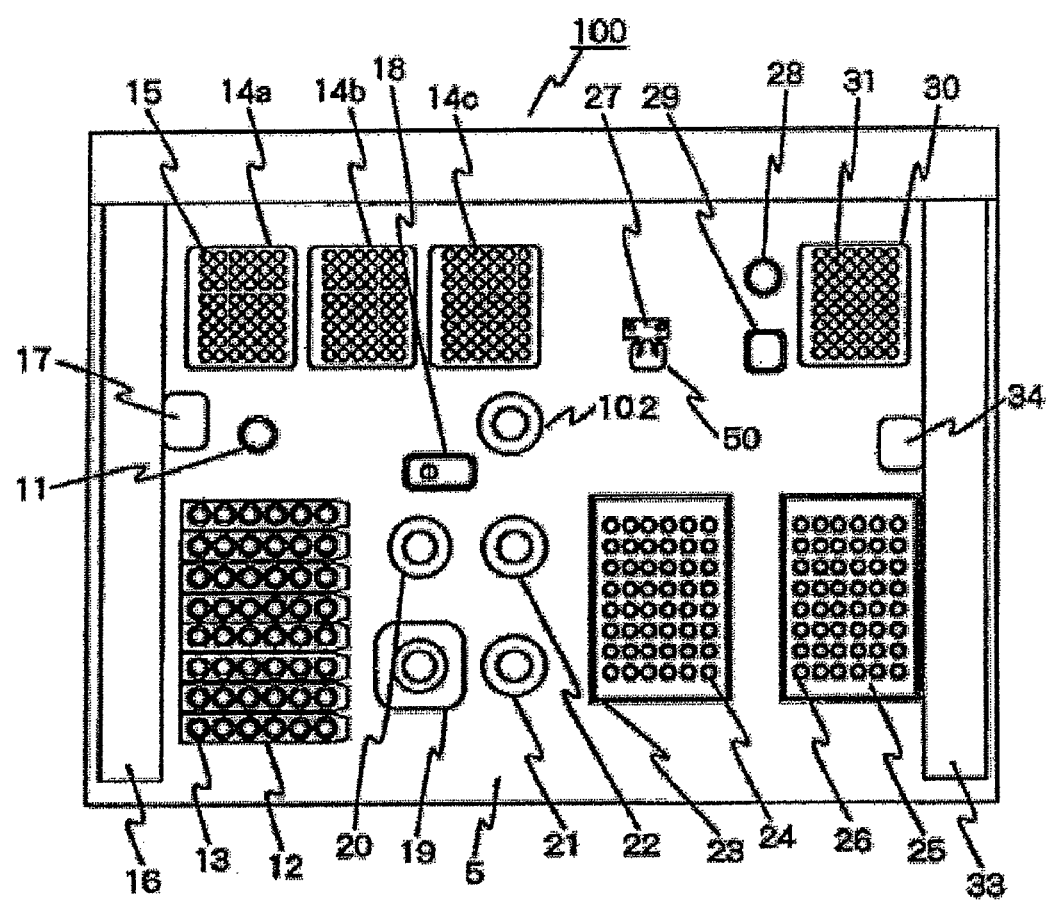
FIG. 2 is a plan view showing the nucleic acid purification device, which is the embodiment according to the present invention.
Figure 3:
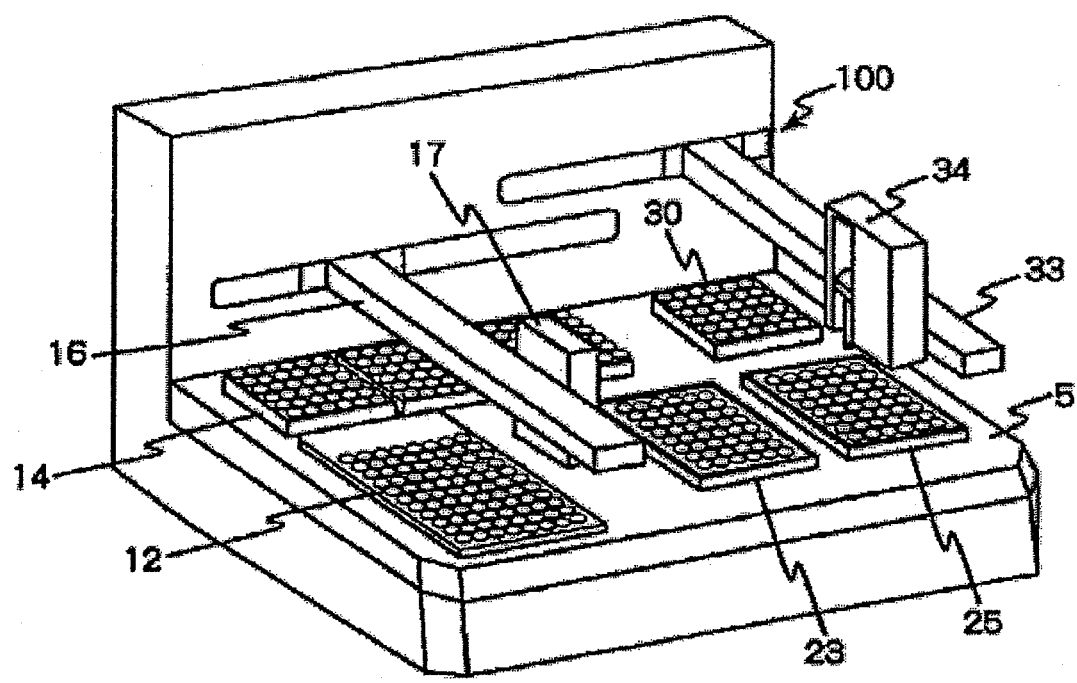
FIG. 3 is a schematic overview showing the nucleic acid purification device shown FIG. 2.
Figure 4:
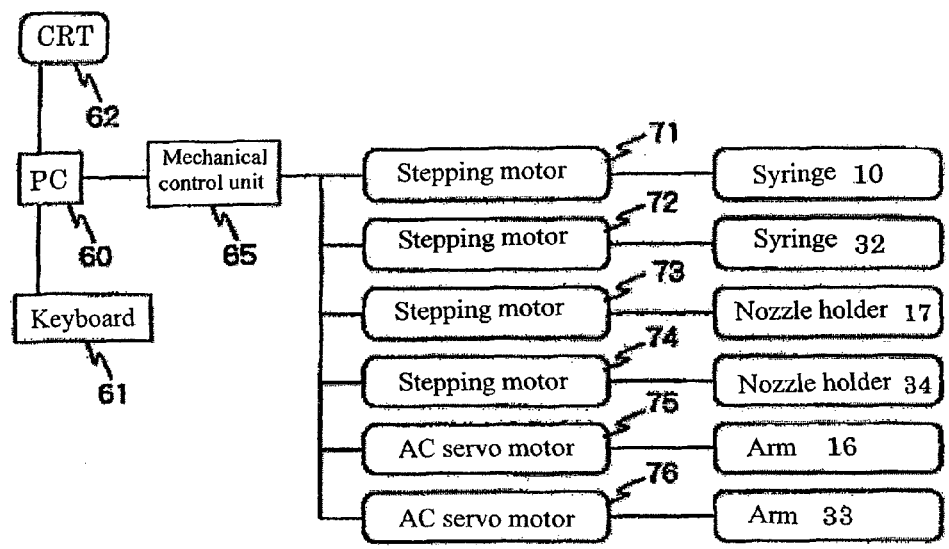
FIG. 4 is a block diagram illustrating an electric system of the embodiment shown in FIG. 2.
Figure 5:
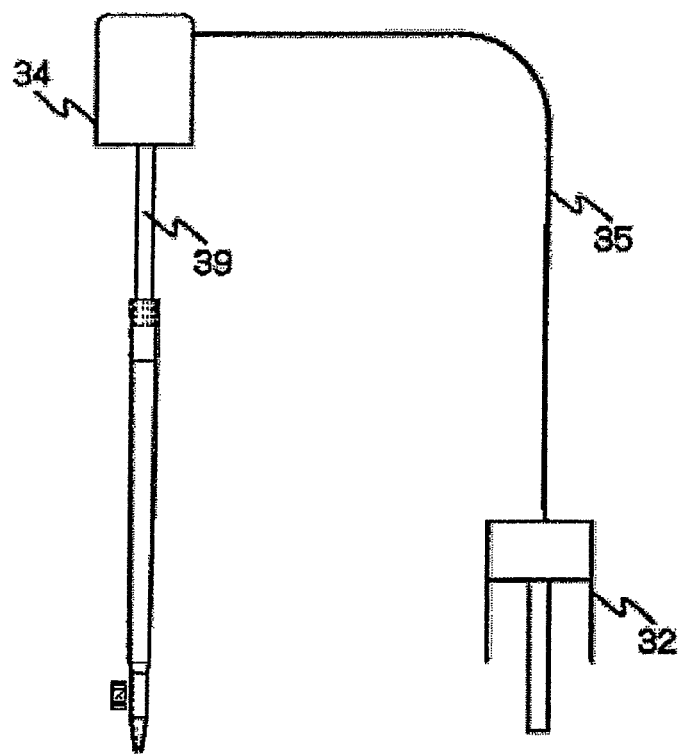
FIG. 5 is a view illustrating a dispenser with the nucleic acid capturing tip attached in the embodiment shown in FIG. 2.
Figure 6:
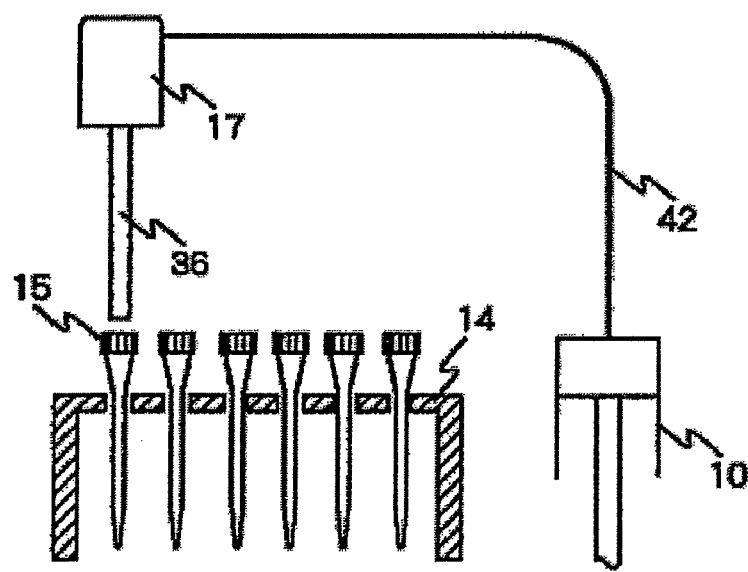
FIG. 6 is a view illustrating the operation of attaching the tip to a nozzle in the embodiment shown in FIG. 2.
Figure 7:
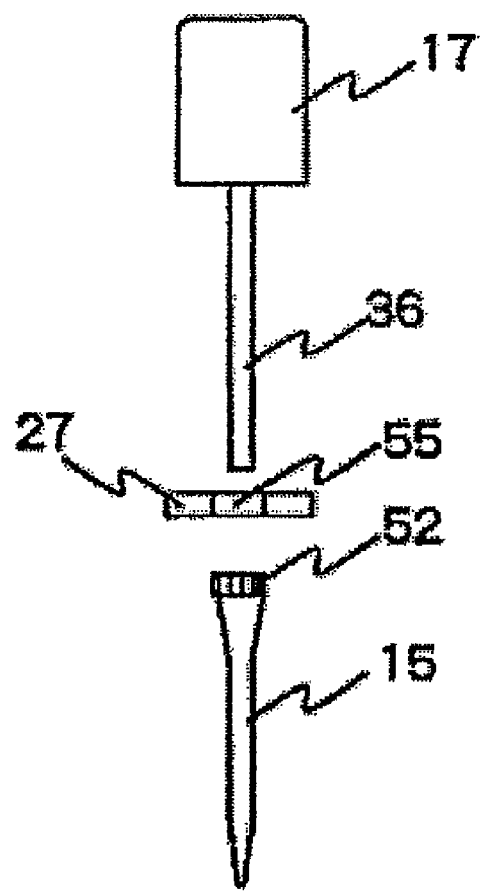
FIG. 7 is a view illustrating the operation of removing the tip from a nozzle in the embodiment shown in FIG. 2.

Next, referring to FIGS. 2 to 7, a nucleic acid purification device used in combination with the nucleic acid capturing tip is described. FIG. 2 is a plan view showing the instrument according to a preferred embodiment, FIG. 3 is its schematic overview, FIG. 4 is a block diagram of an electric system, FIG. 5 id schematic overview of a dispenser with the nucleic acid capturing tip attached, FIG. 6 is a view illustrating the operation of attaching the liquid dispensing tip, and FIG. 7 is a view illustrating the operation of removing the tip.

In FIGS. 2 and 3, the nucleic acid purification device 100 has two arms 16 and 33 capable of moving horizontally (in the X direction). At one arm 16 of two arms, a nozzle holder 17 supporting a dispensing nozzle 36 (FIG. 6) is disposed so that it can move horizontally (in the Y direction) along the length of the arm 16. At another arm 33, a nozzle holder 34 supporting a movable liquid discharge nozzle 39 (FIG. 5) is disposed so that it can move horizontally (in the Y direction) along the length of the arm 33. Both the nozzle holders 17 and 34 can move vertically (in the Z direction) relative to their corresponding arms 16 and 33. Since the horizontal moving area of the arm 16 overlaps partially over that of the arm 33, the arms are disposed at different heights.

On the working plane 5 of a main body stand, three tip racks 14a, 14b, and 14c, each of which mounts a large number of unused dispensing tips 15 are set in a given area. As shown in FIG. 6, these tip racks 14 have bores, into which individual dispensing tips 15 are inserted, wherein the tip racks 14 have a box shape having a height to the extent that the tips do not come into contact with the working plane 5 or the tip rack bottom. The individual tip racks 14a, 14b, and 14c can support up to 48 dispensing tips 15.

In addition, on the working plane 5, a tip rack 30 mounting a large number of unused nucleic acid capturing tips 31 is disposed in a given area. The tip rack 30 has the same shape as that of the tip racks 14 described before. In this example, up to 48 nucleic acid capturing tips 31 can be supported on the tip rack 30.

On the working plane 5, sample racks 12, which support a plurality of sample vessels 13 with the sample to be processed, namely the sample containing nucleic acids therein, are set in a given area. In this example, the individual sample racks 12 can support six sample vessels 13. Alternatively, the individual sample racks 12 can support eight or more sample vessels.

In addition, on the working plane 5, vessel racks 23 supporting a large number of unused processing vessels 24 are set in a given area. The vessel racks 23 can support up to 48 unused processing vessels 24. Besides, on the working plane 5, the vessel racks 23 supporting a large number of unused purification vessels 26 are set in a given area. These purification vessels are used to collect the purified solutions containing nucleic acids for each sample. In this example, vessel racks 25 can support up to 48 purification vessels 26.

On the working plane 5, there are disposed a liquid receiving unit 11, which receives water discharged from dispensing nozzles 36 during priming and play a role of a home position for the dispensing nozzles 36, a cleaning unit 18 for cleaning the dispensing tips 15 for dispensing the solution, a tip detaching device 27 for detaching the dispensing tips 15 attached to the dispensing nozzles 36 and the nucleic acid capturing tips 31 attached to movable liquid suction/discharge nozzles 39 from their corresponding nozzles, a liquid receiving unit 28, which receives water discharged from movable liquid suction/discharge nozzles 39 during priming and can play a role of a home position for the movable nozzles 39, and a waste outlet 29 for discharging wastewater discharged from the nucleic acid capturing tips 31.

In addition, at the individual given positions on the working plane 5, a third reagent bottle 19 used in Step 3a, a fifth reagent bottle 20 used in Step 5, a first reagent bottle 21 used in Step 1, a fourth reagent bottle 102 used in Step 4, a second reagent bottle 22 used in Steps 2a and 2b, and others are set.

A syringe pump 10 shown in FIG. 6 and a syringe pump 32 shown in FIG. 5 are disposed on the main body stand, separately and each of them controls the operations of aspirating and discharging liquid individually. As shown in FIG. 6, The dispensing nozzles 36 supported by the nozzle holders 17 communicate to a liquid discharging syringe pump 10 via a flexible tube 42. Deionized water is filled insides of the dispensing nozzles 36 and the tube 42 and the syringe pump 10 is connected to a deionized water source, not shown. As shown in FIG. 5, the movable nozzles 39 supported by the nozzle holders 34 are connected to the syringe pump 32 via a flexible tube 35. Deionized water is filled insides of the movable nozzles 39 and the tube 35 and the syringe pump 32 is connected to a deionized water source, not shown.

Attachment of the dispensing tips 15 to the dispensing nozzles 36 for connecting between them and the attachment of nucleic acid capturing tips 31 to the movable nozzles 39 for connecting between them are achieved by lowering the individual nozzles until their tips fit to the nozzle tips on their associated tip racks 14 and 30. To detach the dispensing tips 15 connected to the dispensing nozzles 36 and the nucleic acid capturing tips 31 connected to the movable nozzles 39 from their nozzles, the tip detaching device 27 is used. As shown in FIGS. 2 and 7, the tip detaching device 27 has a plate member at a given height, on which there is formed a slit 55 with a width smaller than the outer diameters of the heads 52 of the dispensing tips 15 and the heads 54 of the nucleic acid capturing tips 31 and larger than the outer diameters of the dispensing nozzles 36 and movable nozzles 39. With the heads 52 and 54 of the tips at lower positions than that of the slit 55, the nozzles 36 and 39 are moved horizontally so that it enters into the slit, and the nozzle holders 17 and 34 are raised so that the heads 52 and 54 come into contact with the bottom of the plate member, and they are further raised to slip down the tips 15 and 31. The tips slipped down from nozzles fall into a tip discharging outlet 50 (FIG. 2) and are collected in a collection box, not shown.

FIG. 4 shows the configuration of an electric system of the nucleic acid capturing instrument in FIG. 2. To a personal computer (PC) 60 serving as an operation controller, a keyboard 61 for providing a control panel, from which operation conditions and sample information are inputted, a CRT 62 acting as a display device for displaying entered information, warning information, and others; a mechanical controller 65 for controlling individual mechanical systems of the instrument; and others are connected. The mechanical controller 65 controls a stepping motor 71 for driving a piston causing the syringe pump 10 to aspirate and discharge liquid, a stepping motor 72 for driving a piston causing the syringe pump 32 to aspirate and discharge liquid, a stepping motor 73 for causing the nozzle holders 17 to move vertically and horizontally, a stepping motor 74 for causing the nozzle holders 34 to move vertically and horizontally, an AC servo motor 75 for moving the arm 16 horizontally, an AC servo motor 76 for moving the arm 33 horizontally, and others. The individual parts of the instrument for purification are operated according to a given program.

Using the nucleic acid capturing tips with different average interval among the solid phases to be used shown in FIG. 1, the following describes the experimental example on collecting DNA of hepatitis C virus (HCV) in serum using the nucleic acid purification device shown in FIG. 2. The sample to be processed was prepared so that 100 IU/mL HCV could be achieved in the HCV-negative serum from the secondary standard HCV-positive serum valued with WHO International Standard and then dispensed into the sample vessels 13 shown in FIG. 2. Automatic operation of the device shown in FIG. 2 allowed the arm 16 and the nozzle holders 17 to attach the dispensing tips 15, 200 μL of sample was aspirated from the sample vessels 13, and dispensed into the processing vessels 24. After the sample was dispensed, the arm 16 and the nozzle holders 17 automatically removed the used dispensing tips 15 taking advantage of the action of the tip detaching device 27. Then, the arm 16 and the nozzle holders 17 automatically attach new dispensing tips 15, 700 μm of first reagent was aspirated from the first reagent bottle 21 and discharged into the processing vessels 20 from which the sample was dispensed, the liquid was repeatedly aspirated and discharged five times, the whole amount of liquid was discharged into the processing vessel 24, and left for 10 minutes as it was. Note that for the first reagent described herein, a MES (2-morpholino-ethanesulfonic acid, Dojin Chemical Laboratories, Inc.) buffer solution containing 2% Triton X-100 (LKB) and 5.5 mol/L guanidine thiocyanate (Wako Pure Chemical Industries, Ltd., for biochemical use) was used.

After the liquid being discharged, the arm 16 and the nozzle holders 17 automatically removed the used dispensing tips 15 by taking advantage of the action of the tip detaching device 27. After a given time had passed, the arm 16 and the nozzle holders 17 attached new dispensing tips 15, 100 μL of second reagent was aspirated from the second reagent bottle 22, discharged into the processing vessel 24 with the mixture of the sample and the first reagent filled, the liquid was repeatedly aspirated and discharged five times, and then the whole amount of liquid was discharged into the processing vessel 24. Note that for the second reagent described herein, a MES (Dojin Chemical Laboratories, Inc.)) buffer containing 1% TritonX-100 (LKB) and 5.0 mol/L guanidine thiocyanate (Wako Pure Chemical Industries, Ltd., for biochemical use) was used.

Meanwhile, the arm 33 and the nozzle holders 34 attached the nucleic acid capturing tips 31 and the mixture of the sample, the first reagent, and the second reagent was aspirated from the processing vessel 24 by taking advantage of the action of the syringe 32.

After the mixture being aspirated, the aspirated mixture was discharged into the processing vessel 24 up to the level of liquid, at which the mixture did not exceed the blocking member 101b on the upper side of the nucleic acid capturing tips 31, and then the mixture was aspirated down to the level of liquid, at which the mixture did not exceed the blocking member 101a in the lower side of the nucleic acid capturing tips 31. After this suction/discharge operations being repeated ten times, the whole amount of the mixture from the processing vessel 24 was aspirated and then air was aspirated up to the level of liquid, at which the mixture did not the retaining member 101a. Then, under the control of the arm 33 and the nozzle holders 34, the nucleic acid capturing tips 31 moved toward the liquid receiving vessel 29, discharged the aspirated mixture up to the level of liquid, at which the mixture did not exceed the retaining member 101b, and waited for the next operation.

Meanwhile, the arm 16 and the nozzle holders 17 attached new dispensing tips 15, 800 μL of second reagent was aspirated from the second reagent bottle 19 and the whole amount of the reagent was discharged into the processing vessel 24. After the reagent being discharged, the arm 16 and the nozzle holders 17 automatically removed the used dispensing tips 15 by taking advantage of the action of the tip detaching device 27. Meanwhile, under the control of the arm 33 and the nozzle holders 34, the nucleic acid capturing tips 31 moved, the second reagent was repeatedly aspirated and discharged five times in the same manner as that of the mixture, the whole amount of the mixture was aspirated from the processing vessel 24, and air was aspirated up to the level of liquid, at which the mixture did not exceed the retaining member 101a. Then, under the control of the arm 33 and the nozzle holders 34, the nucleic acid capturing tips 31 moved toward the liquid receiving vessel 29, discharged the aspirated second reagent up to the level of liquid, at which the second reagent did not exceed the retaining member 101b, and waited for the next operation.

Meanwhile, the arm 16 and the nozzle holders 17 automatically attached the new dispensing tips 15, 400 μL of third reagent was aspirated the third reagent bottle 19, and the whole amount of third reagent was discharged into the processing vessel 24. After the third reagent being discharged, the arm 16 and the nozzle holders 17 removed the used dispensing tips 15 by taking advantage of the action of the tip detaching device 27. Meanwhile, under the control of the arm 33 and the nozzle holders 34, the nucleic acid capturing tips 31 moved, the third reagent was repeatedly aspirated and discharged three times in the same manner as that of the mixture, and the first cleaning operation was applied. After the first cleaning operation being finished, the whole amount of mixture was aspirated from the processing vessel 24 and then air was aspirated up to the level of liquid, at which the mixture did not exceed the retaining member 101a. Then, under the control of the arm 33 and the nozzle holders 34, the nucleic acid capturing tips 31 moved toward the liquid receiving vessel 29, discharged the whole amount of reagent, and waited for the next operation.

Meanwhile, the arm 16 and the nozzle holders 17 attached the new nucleic acid capturing tips 15, 800 μL of third reagent was aspirated from the third reagent bottle 19, and the whole amount of third reagent was discharged into the processing vessel 24.

Note that for the third reagent described herein, 50% ethanol (Wako Pure Chemical Industries, Ltd., special class of reagent) containing 25 mmol/L potassium acetate (Wako Pure Chemical Industries, Ltd., special class of reagent) was used.

After the third reagent being discharged, the arm 16 and the nozzle holders 17 removed the used nucleic acid capturing 15 by taking advantage of the action of the tip detaching device 27. Meanwhile, under the control of the arm 33 and the nozzle holders 34, the nucleic acid capturing tips 31 moved, the third reagent was repeatedly aspirated and discharged three times, and the second cleaning operation was applied. After the cleaning operation being finished, the whole amount of the mixture was aspirated from the processing vessel 24, and then air was aspirated up to the level of liquid, at which the mixture did not exceed the retaining member 101a. Then, under the control of the arm 33 and the nozzle holders 34, the nucleic acid capturing tips 31 moved toward the liquid receiving vessel 29, discharged the whole amount of aspirated third reagent, and then aspirated and discharged 1 mL of air repeatedly ten times at the same position, and finally waited for the next operation.

The operation related to the third reagent described above was repeated one more time. Note that this cleaning operation may be further repeated as needed.

After the operation with the third reagent being finished, the arm 16 and the nozzle holders 17 automatically attached the new dispensing tips 15, aspirated 200 μL of fourth reagent from the fourth reagent bottle 102, and discharged the whole amount of aspirated fourth reagent into the processing vessel 24.

Note that for the fourth reagent referred to herein, 50 mmol/L potassium acetate (Wako Pure Chemical Industries, Ltd., special class of reagent) was used.

After the fourth reagent being discharged, the arm 16 and the nozzle holders 17 automatically removed the used dispensing tips 15 by taking advantage of the action of the tip detaching device 27. Meanwhile, under the control of the arm 33 and the nozzle holders 34, the nucleic acid capturing tips 31 was moved, the fourth reagent was repeatedly aspirated and discharged three times to rinse the solid phase. After the rinsing operation being finished, the whole amount of liquid was aspirated from the processing vessel 24, and then air was aspirated, under the control of the arm 33 and the nozzle holders 34, the nucleic acid capturing tips 31 moved to the liquid receiving vessel 29, discharged the whole amount of liquid, aspirated and discharged 1 mL of air repeatedly ten times as the same position, and waited for the next operation.

After the rinsing operation with the fourth reagent, the arm 16 and the nozzle holders 17 automatically attached the new dispensing tips 15, 60 µL of fifth reagent was aspirated from the fifth reagent bottle 20, and the whole amount of aspirated fifth reagent discharged into the processing vessel 24.

Note that for the fifth reagent referred to herein, 10 mmol/L bicine (Dojin Chemical Laboratories, Ltd.) buffer (pH 8.5) containing 0.1 mmol/L ethylenediaminetetraacetic acid (Nippon Gene Co., Ltd., for genetic-engineering research use) was used.

After the fifth reagent being discharged, the arm 16 and the nozzle holders 17 automatically removed the used dispensing tips 15 by taking advantage of the action of the tip detaching device 27. Meanwhile, under the control of the arm 33 and the nozzle holders 34, the nucleic acid capturing tips 31 were moved, the fifth reagent was repeatedly aspirated and discharged twenty times, and the nucleic acids were eluted. After the nucleic acids being eluted, the whole amount of liquid was discharged from the nucleic acid capturing tips 31. After the liquid was discharged, under the control of the arm 33 and the nozzle holders 34, the used nucleic acid capturing tips 31 were removed by taking advantage of the action of the tip detaching device 27. Meanwhile, the arm 16 and the nozzle holders 17 automatically attached the new dispensing tips 15, aspirated the whole amount of eluent from the processing vessel 24 and then a slight amount of air, and under the control of the arm 16 and the nozzle holders 17, the dispensing tips 15 moved toward the purified sample vessel 26, and discharged the whole amount of aspirated eluent therefrom into the purified sample vessel 26. After the sample being discharged, the arm 16 and the nozzle holders 17 removed the used dispensing tips 15 by taking advantage of the action of the tip detaching device 27.

The same steps as those mentioned above were followed using the nucleic acid capturing tips with different average intervals among silica wools, which were produced by keeping the amount of solid phase 102 inspirated the nucleic acid capturing tips 31 constant and changing the distance between the retaining member 101a and the retaining member 101b.

The collected samples were evaluated using COBAS AMPLICOR (Roche) and COBAS AMPLICOR HCV v2.0 (Roche) reagents. 48.5 µL of each sample collected, 41.7 µL of HCV Master Mix v 2.0, 8.3 µL of HCV Manganese reagent, and 1.5 µL of HCV Internal Control v 2.0 L were mixed, the operation was performed in accordance with the procedure document supplied with a reagent kit, and a HCV assay was made on the collected samples. The result of the assay was shown in FIG. 8.

Figure 8:
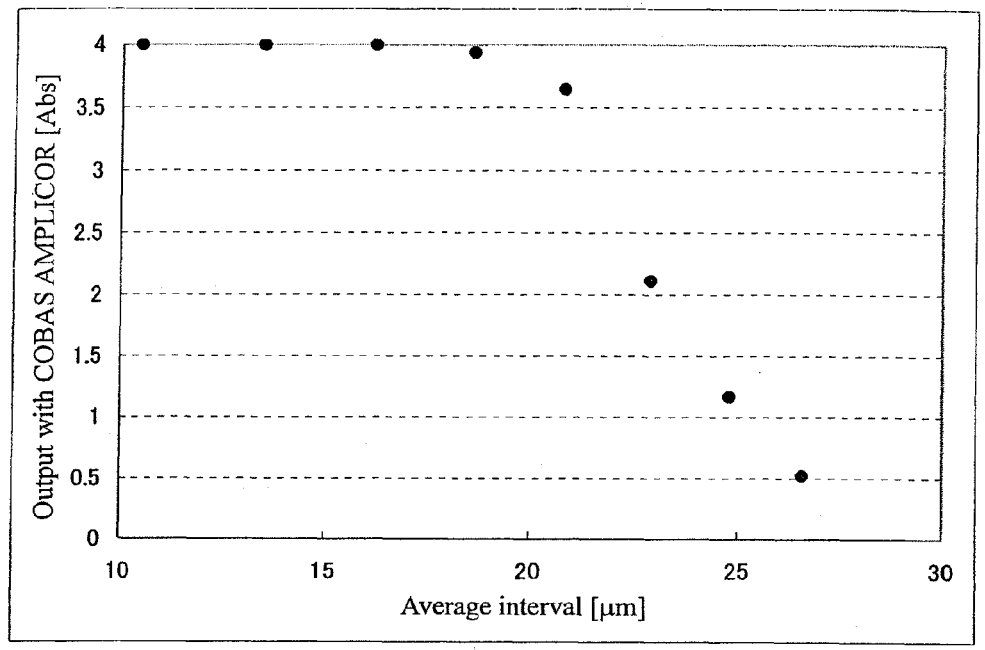
FIG. 8 is a graph showing the result from Mode 1 of the embodiment according to the present invention.

As known from FIG. 8, as the average interval among the solid phases increases, the output of the absorbency of COBAS AMPLICOR reduces in relation to the collected HCV samples of the same concentration. This means that as the average interval among the solid phases increased, the amounts of collected HCV samples reduced, suggesting that in the case of the average interval being 21 µm or more, collection efficiency noticeably may decrease. Note that since the absorbency of COBAS AMPLICOR is indicated as "*.***" when it exceeds 4.000, the absorbency was calculated herein assuming that it was 4.000. An average flow rate of solution was measured when the nucleic acid capturing tips 31 having the average space mentioned above aspirated 1 mL of solution. The result of the measurement was shown in FIG. 9.

Figure 9:
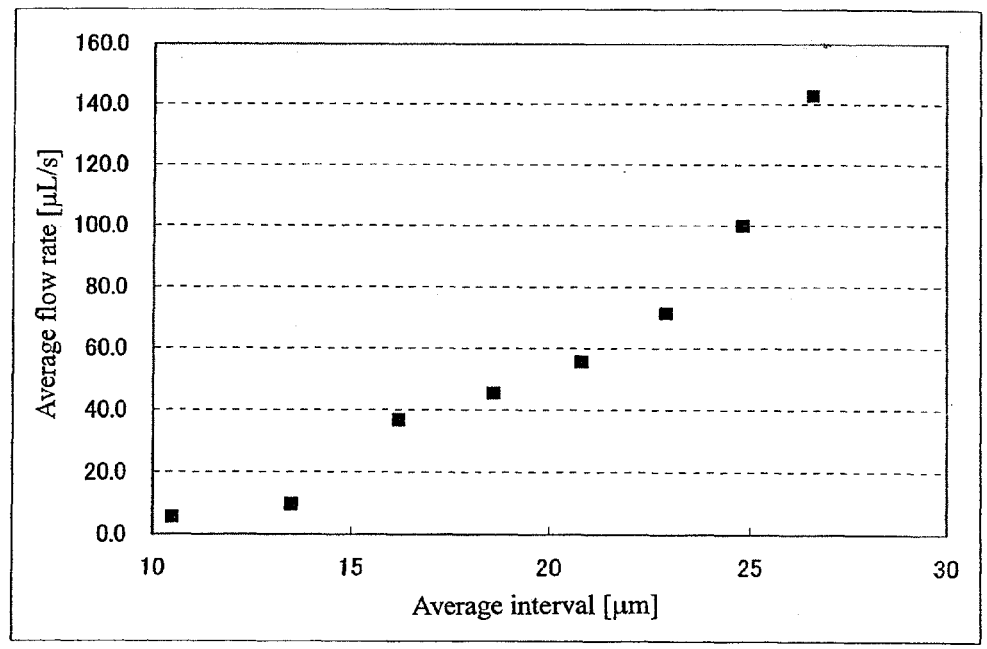
FIG. 9 is a graph showing the result from Mode 1 of the embodiment according to the present invention.

As known from FIG. 9, as the average among the solid phases decreases, the average flow rate reduces. This means that if the average interval is decreased, the waiting time for aspirating or discharging the solution increases, suggesting that a decrease in average interval may increase the processing time required by the device for each sample, which leads to a reduction in operating performance of the device.

As known from FIGS. 8 and 9, the nucleic acid capturing tips shown in FIG. 1 and the device shown in FIG. 2 can collect HCV genes practically to avoid this problem and the desirable average interval for the nucleic acid capturing tips is any of distances ranging from 13 to 21 µm.

Next, the experimental example on collecting the hepatitis B virus (HBV) genes in serum by the nucleic acid purification device shown in FIG. 2 with the chaotropic reagent replaced with other substance.

The nucleic acid capturing tips 31 having a structure shown in FIG. 1 and the average interval among silica wools of 16 µm were produced. With the same configuration of device as that of the nucleic acid purification device 100 shown in FIG. 2, the compositions of the reagents inspirated the first reagent bottle 21 and the second reagent bottle 22 were changed to the MES (Dojin Chemical Laboratories, Ltd.) buffer containing 2% TritonX-100, 6 mol/L guanidine hydrochloride for the first reagent and the MES (Dojin Chemical Laboratories, Ltd.) buffer containing 5 mol/L guaniginate hydrochloride (Wako Pure Chemical Industries, Ltd., for biochemical use) for the second reagent. For the reagents to be used in Steps 3, 4, and 5, the reagents of the same compositions as those used in collecting the HCV genes mentioned earlier.

For samples to be processed, serum, which had positive reaction to an anti-HBV antibody, was used. With the above-mentioned nucleic acid capturing tips 31 combined with the reagents to be used in Steps 1, 2, 3, 4, and 5, the HBV genes were collected by causing the device to operate in the same manner as that in collecting HCV genes mentioned above. The time require for gene collection was about 20 minutes.

To compare the states of gene collection among the method according to the present invention and a prior method, genes were collected by the existing method described in "Protein, Nucleic Acid, Enzyme, 41 (5), 458-459 (1996)" The time required for gene collection was one and a half days.

In relation to the collected samples, an attempt was made to amplify a specific 414 base in the HBV genes using a reagent kit for PCR use made by Takara Shuzo, Co. and an amplification primer synthesized by Sawady Technology in our commission. In the PCR processing step, using The TP3000 (Takara Shuzo, Co., Ltd.) gene amplification system, first thermal denaturation was applied to the samples at 94° C. for three minutes, and second thermal denaturation at 94° C. for 30 seconds, annealing at 55° C. for 30 seconds, and stretch reaction at 72° C. for 30 seconds were repeated forty-five times, and finally they were heated at 72° C. for 10 minutes. After PCR processing being finished, electrophoresis was applied to some of the processed samples in 3% agarose gel and then fluorescent-stain was performed on them with SYBR Greenl (FMC Bioproducts). The result showed that the same level of PCR amplified band as that of the prior method was obtained. This suggests that the target genes could be collected at the same level of collection efficiency as that of but for a shorter time period than the prior method.

Next, the experimental example on collecting both the HBV and HCV genes coexisting in serum by the nucleic acid purification device shown in FIG. 2.

The nucleic acid capturing tips 3 having a structure shown in FIG. 1 and the average interval among the solid phases of 16 μm were produced. The samples to be processed were prepared so that the concentration of each virus in the mixture of two types of virus were two times of that of the experiment mentioned earlier.

The genes were collected with the same compositions of the reagents and in the same device operation as those in collecting HCV genes mentioned above with an exception of only the amount of the Step 5 reagent being changed from 60 μl to 120 μl.

48.5 μL of collected samples were used in detecting HCV genes with COBAS AMPLICOR while 50 μL of them were used in detecting HBV virus genes by applying PCR processing mentioned earlier. In this experiment, each type of genes could be collected from the samples containing two types of coexisting virus genes at the same efficiency as those in collecting these genes for each of two types. This suggests that not only the coexisting virus genes can be collected together but also the nucleic acids with different characteristics such as RNA (ribonucleic acid) and DNA (deoxyribonucleic acid) can be collected together.

The invention claimed is:

1. A nucleic acid collecting method using nucleic acid capturing tips attached to a device capable of aspirating and discharging a liquid by changing a pressure applied, the nucleic acid capturing tips having silica-containing fibrous solid phases enclosed therein in such a state that the silica-containing fibrous solid phases may come into contact with a liquid phase, the silica-containing fibrous solid phases having water-flowing regions, wherein at the water-flowing regions, the average interval among the silica-containing fibrous solid phases is 13-21 μm, the method comprising:
    a first step (Step 1) for mixing a first reagent for separating nucleic acids from samples with nucleic acid-containing samples to accelerate the separation of the nucleic acids;
    a second a step (Step 2a) for mixing a second reagent with a liquid containing the separated nucleic acids, then aspirating a resultant mixture into the nucleic acid capturing tips by changing the pressure applied, making the mixture into contact with the silica-containing fibrous solid phases, and finally discharging the mixture;
    a second b step (Step 2b) for aspirating the second reagent into the nucleic acid capturing tips by changing the pressure applied, then making the second reagent into contact with the silica-containing fibrous solid phases, and finally discharging the reagent to clean the silica-containing fibrous solid phases;
    a third a step (Step 3a) for aspirating a third reagent into the nucleic acid capturing tips by changing the pressure applied, then making the third reagent into contact with the silica-containing fibrous solid phases, and finally discharging the reagent to remove the first reagent and/or the second reagent remaining in the nucleic acid capturing tips;
    a third b step (Step 3b) for blowing air into the nucleic acid capturing tips to accelerate the removal of the third reagent from the nucleic acid capturing tips;
    a fourth step (Step 4) for aspirating a fourth reagent into the nucleic acid capturing tips by changing the pressure applied, then making the fourth reagent into contact with the silica-containing fibrous solid phases, and finally discharging the reagent to flush out the remaining third reagent; and
    a fifth step (Step 5) for aspirating a fifth reagent into the nucleic acid capturing tips by changing the pressure applied, then making the reagent into contact with the silica-containing fibrous solid phases, and finally discharging the reagent to elute the nucleic acids from the solid phases.

2. A nucleic acid-capturing method according to claim 1, wherein the silica-containing fibrous solid phases are silica wools.

3. A nucleic acid collecting method, using nucleic acid capturing tips having silica-containing fibrous solid phases enclosed therein, for collecting the nucleic acid from a mixture of an accelerating reagent for accelerating the bond of the nucleic acids to the silica-containing fibrous solid phases and the nucleic acids, the method comprising:
    a step for aspirating the mixture into the nucleic acid capturing tips having water-flowing regions composed of silica-containing fibrous solid phases with an average interval of 13-21 μm and discharging the mixture; and
    a step for cleaning the solid phases to which the nucleic acids are bound, with a cleaning reagent for the accelerating reagent by aspiration and discharge while keeping the bond of the nucleic acids to the silica-containing fibrous solid phases.

4. A nucleic acid collecting method according to claim 3, wherein the solid phases are silica wools.

5. A nucleic acid collecting method according to claim 4, wherein the diameter of the silica wools is any of sizes ranging from 6 to 12 μm.

6. A nucleic acid collecting method according to claim 3, further comprising:
    a step for eluting the nucleic acids from the silica-containing fibrous solid phases to which the nucleic acids are bound, with a substance taking an action of eluting the nucleic acids from the solid phases by aspiration and discharge.

7. A nucleic acid collecting method using the nucleic acid capturing tips attached to a device capable of aspirating and discharging a liquid by changing a pressure applied, the nucleic acid capturing tips having silica-containing solid phases made of fibrous substance enclosed therein in such a state that the silica-containing solid phases made of fibrous substance may come into contact with a liquid phase, the silica-containing solid phases made of fibrous substance having water-flowing regions, wherein, at the water-flowing regions, an average flow rate ranges from 10 to 50 μL/s, the method comprising:
    a first step (Step 1) for mixing a first reagent for separating nucleic acids from samples with nucleic acid-containing samples to accelerate the separation of the nucleic acids;
    a second a step (Step 2a) for mixing a second reagent with a liquid containing the separated nucleic acids, then aspirating a resultant mixture into the nucleic acid capturing tips by changing the pressure applied, making the mixture into contact with the silica-containing solid phases made of fibrous substance, and finally discharging the mixture;
    a second b step (Step 2b) for aspirating the second reagent into the nucleic acid capturing tips by changing the pressure applied, then making the second reagent into contact with the silica-containing solid phases made of fibrous substance, and finally discharging the reagent to clean the silica-containing solid phases made of fibrous substance;

a third a step (Step 3a) for aspirating a third reagent into the nucleic acid capturing tips by changing the pressure applied, then making the third reagent into contact with the silica-containing solid phases made of fibrous substance, and finally discharging the reagent to remove the first reagent and/or the second reagent remaining in the nucleic acid capturing tips;

a third b step (Step 3b) for blowing air into the nucleic acid capturing tips to accelerate the removal of the third reagent from the nucleic acid capturing tips;

a fourth step (Step 4) for aspirating a fourth reagent into the nucleic acid capturing tips by changing the pressure applied, then making the fourth reagent into contact with the silica-containing solid phases made of fibrous substance, and finally discharging the reagent to flush out the remaining third reagent; and a fifth step (Step 5) for aspirating a fifth reagent into the nucleic acid capturing tips by changing the pressure applied, then making the reagent into contact with the silica-containing solid phases made of fibrous substance, and finally discharging the reagent to elute the nucleic acids from the solid phases.

8. A nucleic acid-capturing method according to claim 7, wherein the silica-containing solid phases made of fibrous substance are silica wools.

9. A nucleic acid collecting method using nucleic acid capturing tips having silica-containing fibrous solid phases enclosed therein, for collecting the nucleic acid from a mixture of an accelerating reagent for accelerating the bond of the nucleic acids to the silica-containing fibrous solid phases and the nucleic acids, the method comprising:

a step for aspirating the mixture into the nucleic acid capturing tips having water-flowing regions composed of silica-containing fibrous solid phases and discharging the mixture, wherein an average flow rate of the mixture is any of rates ranging from 10 to 50 µL/s; and a step for cleaning the solid phases to which the nucleic acids are bound, with a cleaning reagent for the accelerating reagent by aspiration and discharge while keeping the bond of the nucleic acids to the silica-containing fibrous solid phases.

10. A nucleic acid collecting method according to claim 9, wherein the silica-containing fibrous solid phases are silica wools.

11. A nucleic acid collecting method according to claim 10, wherein the diameter of the silica wools is any of sizes ranging from 6 to 12 µm.

12. A nucleic acid collecting method according to claim 9, comprising:

a step for eluting the nucleic acids from the silica-containing fibrous solid phases to which the nucleic acids are bound, with a substance taking an action of eluting the nucleic acids from the silica-containing fibrous solid phases by aspiration and discharge.

* * * * *